United States Patent [19]

Hu et al.

[11] Patent Number: 5,032,666
[45] Date of Patent: Jul. 16, 1991

[54] AMINE RICH FLUORINATED POLYURETHANEUREAS AND THEIR USE IN A METHOD TO IMMOBILIZE AN ANTITHROMBOGENIC AGENT ON A DEVICE SURFACE

[75] Inventors: Can B. Hu, Irvine, Calif.; Donald D. Solomon, Spring Valley, Ohio

[73] Assignee: Becton, Dickinson and Company, Franklin Lakes, N.J.

[21] Appl. No.: 368,013

[22] Filed: Jun. 19, 1989

[51] Int. Cl.$^5$ .............................................. C08G 18/30
[52] U.S. Cl. ..................................... 528/70; 604/264; 528/61
[58] Field of Search .................................... 528/61, 70

[56] References Cited

U.S. PATENT DOCUMENTS 3,870,748  3/1975  Katsushima et al. ............... 528/70
3,972,856  8/1976  Mitsch et al. ....................... 528/70
4,054,592  10/1977  Dear et al. .......................... 528/70
4,158,672  6/1979  Dear et al. .......................... 528/70

Primary Examiner—John Kight, III
Assistant Examiner—Dennis R. Daley
Attorney, Agent, or Firm—Richard E. Brown; Arthur D. Dawson

[57] ABSTRACT

A thermoplastic polyurethaneurea having free amino groups is the reaction product of a diisocyanate, a fluorinated polyol, a non-fluorinated polyol and a polyamine. The invention includes a shaped polymeric support structure having the thermoplastic polyurethaneurea coated thereon and a medical article comprising the coated support and heparin covalently bonded to the free amino groups of the coated support. In another aspect of the invention, a method for preparing the heparinized medical article is provided.

6 Claims, No Drawings

AMINE RICH FLUORINATED POLYURETHANEUREAS AND THEIR USE IN A METHOD TO IMMOBILIZE AN ANTITHROMBOGENIC AGENT ON A DEVICE SURFACE

BACKGROUND OF THE INVENTION

1. Field of the Invention

This invention relates to biomedical devices, and more specifically relates to a method for covalent immobilization of an antithrombogenic agent onto a substrate.

2 Background of the Invention

Extensive investigations have been undertaken over many years to find materials that will be biologically and chemically stable toward body fluids. This area of research has become increasingly important with the development of various objects and articles which must be in contact with blood, such as artificial organs, vascular grafts, probes, cannulas, catheters and the like.

Synthetic plastics have come to the fore as preferred materials for such articles. However, these materials have the major drawback of being thrombogenic. Thrombogenicity has conventionally been counteracted by the use of anticoagulants such as heparin. Various procedures for attachment of heparin to otherwise thrombogenic polymeric surfaces have been disclosed. In one method taught by R. I. Leininger and G. A. Grode, U.S. Pat. No. 3,457,098, a quaternary amine is incorporated into an epoxy resin. Subsequent exposure to sodium heparinate dissolved in water then results in ionically bound heparin. The polymer systems are essentially rigid epoxy resins which are not suitable for forming medical devices such as catheters or other devices requiring extrusion. These polymers also are not appropriate where flexibility in the device is required.

Leininger et al., in U.S. Pat. No. 3,617,344 discloses a method in which a polymeric surface is chemically modified to include a chloromethyl group. Amination of the chloromethyl group provides a quarternary ammonium halide. Reaction of the halide with sodium heparin results in ionic bonding of the heparin to the surface.

A related approach for ionic binding has been described by Eriksson et al. in U.S. Pat. No. 3,634,123. An article having a plastic surface is heated to near or above its softening point in an aqueous solution of a cationic surface active agent, such as a long chain alkylamine or alkylenediamine hydrohalide. The solution is preacidified to a pH of 7.0 or lower. Subsequent digestion of the plastic article with an aqueous solution of heparin results in an article having about 0.1 International Unit of heparin thereon.

Williams et al., in U.S. Pat. Nos. 4,349,467 and 4,613,517 disclose modifications of the surface active agent-heparin method. The former patent discloses that higher quantities of heparin are attached to a plastic surface by using more concentrated solutions of heparin. The latter patent discloses treating a polymeric surface with a plasma, digesting the plasma-treated surface with a quaternary ammonium salt, reacting the salt with sodium heparin, and crosslinking the heparin with glutaraldehyde.

Covalent conjugation of heparin to a polymeric article coated with an amine-rich surface is disclosed in U.S. Pat. No. 4,521,564 to Solomon et al. In an improvement disclosed by Hu et al. in U.S. Pat. No. 4,720,512, fluorine atoms are plasma deposited onto the amine-rich surface of Solomon et al. prior to heparinization.

Polyurethanes containing segments derived from both perfluoroalkyl substituted diols and polysiloxane diols are disclosed by Mueller in U.S. Pat. No. 4,098,742.

U.S. Pat. No. 4,810,749 to Pinchuk discloses fluorinated polyurethanes prepared from fluorinated polysiloxane diols.

Copending application Ser. No. 173,892, of common assignee herewith discloses fluorinated polyetherurethanes and medical devices fabricated therefrom.

While significant advances have been made toward antithrombogenic surfaces for fabrication of medical devices, further improvements are needed. In particular, materials having surfaces that are essentially nonthrombogenic for use in devices which will be in contact with blood for prolonged periods are needed. It is toward fulfillment of this need that this invention is directed.

SUMMARY OF THE INVENTION

A thermoplastic fluorinated polyurethaneurea (hereinafter FPUU) having free amino groups is the reaction product of a diisocyanate, a fluorinated polyglycol (hereinafter FPG), a polyamine, and another glycol such as a polyalkyleneoxide polyol (hereinafter PAO) or a polyester polyol. Preferred FPUUs of the invention are prepared from 4,4'-diphenylmethane diisocyanate (MDI) and polytetramethylene ether glycol (PTMEG) and include 0.1% of more of the FPG.

Another aspect of the invention is a medical device which includes a polymeric support structure having a coating of the FPUU thereon and an antithrombogenic agent covalently bonded to the FPUU coating through the free amino groups. The preferred antithrombogenic agent is heparin and the preferred device is a catheter.

The invention includes a method to prepare the hemocompatible medical device. In the preferred method, an FPUU prepolymer having terminal isocyanate groups is coated onto the support structure having the desired shape of the medical device. The free isocyanate groups are then reacted with the polyamine to introduce free amino groups to the FPUU on the shaped support structure. The free amino groups are then reacted with aldehyde-activated heparin.

The fluorine atoms of the FPUU introduce hydrophobicity to the device surface whereby the antithrombogenic effect of the heparin is enhanced. Further, introduction of the fluorine atoms by inclusion of a fluorinated polyol in the FPUU chain is an operationally simple process in contrast to the prior art method in which fluorine atoms are introduced in a separate plasma deposition step requiring complex and costly plasma generating equipment.

Thus, the invention provides an amine rich FPUU and a medical device including the FPUU having heparin covalently bonded to the device surface. The device has excellent biological and chemical stability toward body fluids, in particular toward blood. Because the heparin is covalently bonded to the surface, it is not washed off the device surface by flowing blood so that the device retains its antithrombogenic character substantially permanently.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

The FPUU coatings of the invention which are suitable for heparinization include three essential components, a diisocyanate, an FPG and a polyamine. Preferred coatings additionally contain a nonfluorinated polyol.

Suitable diisocyanates are aromatic diisocyanates such as MDI, 3,3'-diphenylmethanediisocyanate, alicyclic diisocyanates such as isophorone diisocyanate and 4-4'-dicyclohexylmethanediisocyanate, and aliphatic diisocyanates, as, for example, hexamethylene diisocyanate. The most preferred diisocyanate is MDI.

The quantity of isocyanate which may be used may be expressed in terms of the conventional isocyanate index. The index is preferably kept below 100 to maximize the number of free amino end groups retained on the FPUU for heparin attachment. Thus, the isocyanate index may be about 40-99, preferably about 65 to 95, most preferably about 75 to 90.

Any polyether glycol having from about 10 to 70% fluorine by weight may serve as the FPG. All percentages herein are by weight unless otherwise stated. Preferred FPGs have from about 30-60% by weight of fluorine in pendant perfluoroalkyl groups and are of the following general formula:

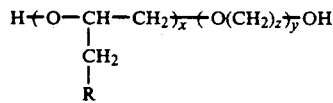

wherein R may be a perfluorinated alkyl group having from about 1 to 12 carbon atoms, x may be from about 1 to 4, y may be from about 0 to 20 and z may be from about 2 to 5. In preferred FPGs, R may be from about 4 to 10 carbon atoms. Most preferably, R is a perfluorohexyl group. Fluorinated polyols of the invention are available from E. I. DuPont de Nemours Co., Wilmington, Del.

The PAO may be, for example, polyethylene glycol, polypropylene glycol, PTMEG and the like or mixtures thereof. Preferred polyols are PTMEG having a molecular weight of from about 500 to about 5000. The most preferred PAO is a PTMEG having a molecular weight of about 1000 to 2000. Such polyols are commercially available from DuPont as Terathane 1000 and 2000 respectively.

If it is desired to include a polyester glycol in the nonfluorinated glycol component of the FPUU, suitable glycols are, for example, polyethylene adipate and polycaprolactone.

The percentage of the FPG in the total glycol content may be about 0.1% to 100%. Preferably the weight percentage of the FPG is about 5 to 40%.

The polyamine component may be any material or mixture of materials which confers free amino end groups to the FPUU of the invention. Suitable polyamines are, for example, diamines of about 2 to 20 carbon atoms. Exemplary of suitable diamines are hexamethylenediamine, octamethylenediamine, dodecamethylenediamine and 2-methylpentamethylenediamine. Diaminopolyethers may also be used. Exemplary of suitable diaminopolyethers is Jeffamine ED 600, a poly(oxyethylene) based diamine available from Texaco Chemical Co., (Bellair, Tex. 77401).

The weight percentage of the polyamine in the FPUU may be from about 1 to 70, preferably about 5 to 30% of the total weight of the FPUU.

The FPUU of the invention may be prepared by a one-step polymerization method or, preferably by a two-step method proceeding through a prepolymer. In the one-step method, the glycol mixture and polyamine are combined and, with vigorous agitation, the diisocyanate is added all at once. In the prepolymer method, the glycol mixture is reacted with the diisocyanate to give a prepolymer having terminal isocyanate groups. The isocyanate-terminated prepolymer may then be reacted with the diamine to give an FPUU having amino end groups, or preferably, as described below, the prepolymer may be coated onto the polymeric support structure prior to amination.

It is readily seen that, by either procedure, the fluorine atoms are part of the polyurethaneurea chains in contrast to prior art formulations in which the fluorine atoms are only on the surface of the polymer chains.

The polymeric materials used in the invention as the solid support structure may be selected from a wide range of polymeric materials. The surface of the solid support may or may not be modified depending on each of the individual materials. Illustrative plastic materials useful as the support structure may be selected from the group consisting of polyethylene, polypropylene, polyurethane, polyurethane-silicone copolymer, polyurethaneurea, polycarbonate, silicone rubber, polyester, nylon, natural rubber, polyvinyl chloride, acrylic, polystyrene, copolymers of polycarbonate and silicone rubber and mixtures thereof. The preferred support structure is a polyurethane or polyurethaneurea.

The particular form of the solid support structure does not constitute a critical aspect of this invention other than to serve as a support for further treatment according to the inventive process. Preferably, the support structure is molded, cast or extruded to the desired shape of the final device prior to applying the coating of amine-rich FPUU or isocyanate terminated prepolymer. Most preferably, the support structure is molded into the shape of a catheter, vascular graft or vascular prosthesis.

Any suitable process may be used to coat the polymeric support structure with the amine-rich FPUU. For example, the amine-rich FPUU may be brushed or sprayed onto the support structure. A preferred method is to prepare a solution of the amine-rich FPUU in a suitable solvent, as, for example, alcohol, methylene chloride, tetrahydrofuran, dimethyl sulfoxide N-methylpyrrolidone or dimethyl formamide or mixtures thereof. The support structure may then be dipped or steeped in the solution for about 0.5 to 30 minutes at a temperature of about 0° C. up to the boiling point of the solvent, preferably for about 0.5 to 5 minutes at room temperature. The coating thereby bonds to the support structure surface, and the amino groups provide a site for covalent attachment of the antithrombogenic agent.

Most preferably, the preferred polyurethane or polyurethaneurea support structure is coated by dipping, for about 5 to 30 minutes at a temperature of about 25° to 75° C., preferably about 30° to 70° C., into a solvent solution of the prepolymer having terminal isocyanate groups. In this sequence of reaction steps, bonding of the FPUU to the support structure is enhanced by reaction of some of the isocyanate groups of the prepolymer with the support structure. The coated support structure may then be dipped into a solvent solution of the polyamine for about 15 to 35 minutes at a temperature of about 25° to 60° C., preferably about 40° to 50° C., to react the remaining isocyanate groups with the polyamine to give a support structure having amino end groups for attachment of the antithrombogenic agent.

The support structure coated with amine-rich FPUU as described above may be treated with the antithrombogenic agent. The term antithrombogenic agent as used herein refers to any material which inhibits thrombus formation on the surface of the support structure, such as by reducing platelet aggregation, dissolving fibrin, enhancing passivating protein deposition, or inhibiting one or more steps within the coagulation cascade. Illustrative antithrombogenic materials may be selected from the group consisting of heparin, prostaglandins, sulfated polysaccharides, and mixtures thereof. Heparin is preferred.

Preferably, the antithrombogenic agent may be chemically modified to introduce a functional group for enhancement of covalent bonding to the free amino groups of the FPUU. Activation of the antithrombogenic agent may be performed in various ways, preferably by chemical modification with oxidizing or reducing agents. Most preferably, heparin may be oxidized to give an aldehyde-modified heparin. Reaction of the aldehyde group with the free amino group of the FPUU gives a Schiff's base which may be reduced to covalently bond the heparin to the FPUU.

The aldehyde group of the activated heparin and the amino groups may conveniently be reacted by steeping the support having the amine-rich FPUU thereon in a solution of the activated heparin and the reducing agent. Preferably, the support may be maintained at about 20° to 50° C. in an aqueous solution of about 0.1 to 15% by weight of the aldehyde-modified heparin containing about 1 to 30% sodium cyanoborohydride for about 0.5 to 35 hours.

Upon completion of the antithrombogenic coupling reaction, the surface may be washed with water to remove loosely bound or unreacted antithrombogenic agent. Washing may be optionally performed with an isotonic solution. The quantity of heparin thereby covalently bound to the substrate surface may be from about 10 to 80 $\mu g/cm^2$.

It is believed, although not yet substantiated, that the enhanced antithrombogenic activity of the heparinized device of the invention is due to an enhanced hydrophobic character imparted to the FPUU surface by the fluorine atoms. Thus, the fluorine atoms minimize the interaction of the hydrophilic antithrombogenic group (e.g., heparin molecules) causing the latter to stay extended outwardly from the substrate surface, thereby making them more available for contacting blood and consequently more active in preventing thrombus formation.

It should be recognized that the products of this invention are useable in a wide variety of devices designed for contacting body fluids. Exemplary articles which can be in contact with body fluids such as blood, include artificial organs, vascular grafts, probes, cannulas, catheters, hemodialysis tubing, hyperalimentation catheters and other long-indwelling vascular catheters, and the like. A particularly preferred application, of the products of the invention is in catheter type devices wherein the inventive compositions are coated on either or both of the interior and exterior surfaces of the catheter.

The invention will be further illustrated by the following non-limiting examples.

EXAMPLE I

General Procedure for Preparation of Isocyanate Terminated Prepolymer

Fluorinated polyol was first dissolved in methylene chloride. MDI was then added to the mixture. After fifteen minutes agitation, another polyol, such as polyethylene glycol, polypropylene glycol or polytetramethylene glycol, was added. The temperature of the reaction was controlled at 70°± 10° C. An additional increment of MDI was added to the above mixture with continuous stirring. After two hours agitation, the resin mixture was cooled. Depending on the proportions of polyol and MDI employed, the prepolymer as prepared above may have from about 1 to 20% free isocyanate.

EXAMPLE II

Coating Prepolymer Onto Polymeric Substrate

Samples of polyurethane tubing were dipped into a 40% by weight solution of a prepolymer having 9.5% free isocyanate prepared in accordance with Example I from PTMEG of molecular weight 2000. The tubing was maintained in contact with the prepolymer for 15 minutes under a nitrogen atmosphere, then removed from the solution and the solvent flashed off.

EXAMPLE III

Reacting Prepolymer-Coated Substrate with Polyamine

The tubing coated with isocyanate-terminated prepolymer from Example II was placed in a 25° C. enclosed environment for 30 minutes to flash the solvent. During the flash-off period, the atmosphere was continuously flushed with nitrogen. After 30 minutes, the tubing was transferred to a 20% solution of hexamethylenediamine at 50° C. After five minutes the tubing was removed and placed in a continuous flow water rinse for up to 48 hours to remove any non-covalently bound diamine.

EXAMPLE IV

Preparation of FPUU and Application to Polymeric Substrate

One hundred-fifty (150) mls of methylene chloride was used to dissolve 19 grams of fluoropolyether glycol. In another container, 10.5 grams of MDI was added to 100 ml of 1-methyl-2-pyrrolidinone. The latter was then added to the former. After 15 minutes, 188 grams of PTMO was added. An additional 43 grams of MDI was added and stirred coninuously. After two hours of agitation, the reaction mixture was cooled to about 25° C. 1,6-Hexanediamine in 400 ml of 1-methyl-2-pyrrolidinone was added slowly to the above mixture. An additional 400 ml of 1-methyl-2-pyrrolidinone was then added and the mixture mixed to homogeneiety. A polyurethane tubing was dipped into the homogeneous mixture for one minute, withdrawn and the solvent removed.

EXAMPLE V

A. Preparation of Radiolabeled Aldehyde-Activated Heparin

Seventy-five (75) mls of water were added to a beaker which contained 150 mls of 1% $^3$H-Heparin solution. Then 1.5 grams of sodium acetate was transferred to the beaker. The pH of this solution was adjusted to 4.5 with glacial acetic acid. Sodium periodate (NaIO$_4$) in the amount of 0.075 grams was added and the solution was reacted for 20 minutes in a light protected reaction vessel with constant stirring. At the end of the reaction, 2.26 grams of glycerin was added to neutralize any remaining periodate. The solution was dried down overnight under nitrogen. Then the solution was reconstituted to 2% and the pH of the solution was adjusted to 6.6 by the dropwise addition of 10 N NaOH. The aldehyde activated $^3$H-heparin solution was ready for bonding to the amine compound. It should be noted that other types of radioactive labeled heparin other than $^3$H are useful.

B. Preparation of Aldehyde-Activated Heparin 7.5 grams of heparin was dissolved in 1125 mls of distilled water. Three (3.0) grams of sodium acetate was weighed and transferred to the heparin solution. The pH of this solution was then adjusted to 4.5 with glacial acetic acid. Sodium periodate (NaIO$_4$) was added in the amount of 0.375 grams and the solution was reacted for 20 minutes in a light protected reaction vessel with constant stirring. At the end of the reaction, 11.30 grams of glycerin was added to neutralize any remaining periodate. Then the solution was reconstituted to 2%. The pH of the solution was adjusted to 6.6 by the dropwise addition of 10 N NaOH. The aldehyde activated heparin solution was ready for bonding to the amine compound.

EXAMPLE VI

Heparinization of Amine-Rich FPUU on Substrate Surface

The amine rich substrate from Example III was immersed in a stirred 2% aqueous solution of aldehyde-activated heparin containing 0.025 g of sodium cyanoborohydride at pH 6° and 50° C. for 2 hours. The samples were removed from the bath and placed in a 3 M saline solution for one hour to remove any loosely bonded or absorbed heparin. By conducting an identical experiment with radiolabeled heparin, the quantity of covalently bound heparin may easily be determined.

What is claimed is:

1. A thermoplastic polyurethaneurea having reactive amino groups comprising a product from the reaction of a diisocyanate, a polyamine and a mixture of polyols comprising a fluorinated polyol and a nonfluorinated polyol, said nonfluorinated polyol being selected from the group consisting of a polyalkyleneoxide polyol and a polyesterpolyol.

2. The polyurethaneurea of claim 1 wherein said diisocyanate is selected from the group consisting of 4,4'-diphenylmethane-diisocyanate, 3,3'-diphenylmethane-diisocyanate, 4,4'-dicyclohexylmethane-diisocyanate, isophorone diisocyanate, hexamethylene diisocyanate and mixtures thereof.

3. The polyurethaneurea of claim 1 wherein said fluorinated polyol is selected from the group having the formula

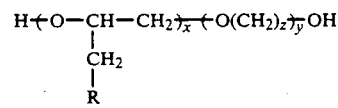

wherein R is a perfluorinated alkyl group having about 1 to 12 carbon atoms, x is about 1 to 4, y is about 0 to 20 and z is about 2 to 5.

4. The polyurethaneurea of claim 1 wherein said polyalkyleneoxide polyol is selected from the group consisting of polytetramethylene ether glycol, polypropylene glycol, polyethylene glycol and mixtures thereof.

5. The polyurethaneurea of claim 1 wherein said polyamine is selected from the group consisting of a diamine having from 2 to 20 carbon atoms and a polyoxyethylene diamine.

6. A thermoplastic polyurethaneurea having reactive amino groups comprising a product from the reaction of 4,4'-diphenylmethane-diisocyanate, a polyamine and a mixture of polyols consisting of a fluorinated polyether polyol and polytetramethylenether glycol.

* * * * *